United States Patent

Cross et al.

[11] Patent Number: 5,171,744
[45] Date of Patent: Dec. 15, 1992

[54] ANTIMUSCARINIC BRONCHODILATORS

[75] Inventors: Peter E. Cross, Canterbury; Alan Stobie, Hambrook, both of England

[73] Assignee: Pfizer Inc., New York, N.Y.

[21] Appl. No.: 598,288

[22] Filed: Oct. 16, 1990

[51] Int. Cl.$^5$ .................... A61K 31/44; C07D 413/00
[52] U.S. Cl. .................... 514/305; 514/826; 546/137
[58] Field of Search ................ 546/137; 514/305, 826

[56] References Cited

U.S. PATENT DOCUMENTS

| | | | |
|---|---|---|---|
| 3,714,357 | 1/1973 | Gueremy | 546/137 X |
| 4,843,074 | 6/1298 | Rzeszotarski et al. | 546/137 X |
| 4,988,691 | 1/1991 | Benelli et al. | 546/137 X |

OTHER PUBLICATIONS

Larsson, et al. "Hydrogen bond . . . ", Acta Pharm. Suecica 11, 304–308, 1974.

*Primary Examiner*—Marianne M. Cintins
*Assistant Examiner*—Catherine S. Kilby Scalzo
*Attorney, Agent, or Firm*—Peter C. Richardson; Paul H. Ginsburg; Grover F. Fuller, Jr.

[57] ABSTRACT

Compounds having the formula:

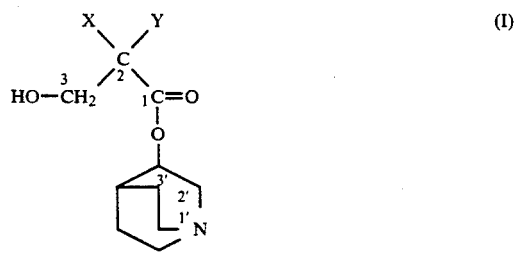

wherein X is either (a) a phenyl group optionally substituted by 1 or 2 substituents each independently selected from halo, $CF_3$, $C_1$-$C_4$ alkyl, $C_1$-$C_4$ alkoxy and hydroxy, or (b) a thienyl group; and Y is an imidazolyl, pyrazolyl, triazolyl or tetrazolyl group optionally substituted by 1 or 2 substituents each independently selected from halo, $CF_3$, $C_1$-$C_4$ alkoxy, hydroxy and amino; and pharmaceutically acceptable salts thereof, are antimuscarinic bronchodilators useful in the treatment of chronic obstructive airways disease and asthma.

11 Claims, No Drawings

ANTIMUSCARINIC BRONCHODILATORS

FIELD OF THE INVENTION

This invention relates to 3-quinuclidinyl propanoates, specifically to certain 3-quinuclidinyl 3-hydroxy-2-heterocyclic-2-(phenyl or thienyl propanoates which are lung-selective antimuscarinic bronchodilators. Thus these compounds are particularly useful in the treatment of chronic obstructive airways disease (COAD) and asthma in mammals, including humans.

BACKGROUND OF THE INVENTION

COAD is a term encompassing conditions which exhibit, to differing extents, several major progressively developing clinicopathological features, namely inflammatory swelling of airway walls, hypertrophy of submucosal glands, and hyperplasia of epithelial secretory cells leading to hypersecretion of viscous mucous which cannot be cleared effectively, progressive increase in irreversible bronchospasm and decrease in lung elastic recoil. This complex pathway results in progressive loss of lung function, with respiratory impairment, increasing morbidity and, finally, death.

Thus COAD, and also asthma, are diseases of reduced lung function in which antimuscarinic bronchodilators are known to improve airway patency. However, existing agents are non-selective for smooth muscle muscarinic sites in lung and this reduces their effectiveness as bronchodilators and leads to unwanted side effects. Sub-types of muscarinic receptor are known to exist in the airways (see P. J. Barnes, P. Minette and J. Maclagan, TIPS, 1988, 9, 412.); $M_1$ receptors are present on sympathetic nerves and parasympathetic ganglia; $M_2$ receptors on pulmonary cholinergic nerves (pre-junctional inhibitory receptors) and $M_3$ receptors are located on smooth muscle (post-junctional receptors). The compounds of the present invention generally have bronchospasmolytic effects at doses which do not significantly affect other tissues such as brain, heart, gastro-intestinal tract, eye and salivary glands. Furthermore, they generally show selectivity for the lung post-junctional $M_3$ receptors as opposed to the pulmonary pre-junctional $M_2$ receptors and cardiac $M_2$ receptors. Therapeutic action at some other smooth muscle sites may be envisaged. For example, the compounds are also likely to be useful in treating urinary incontinence.

SUMMARY OF THE INVENTION

Thus the present invention provides a compound of the formula:

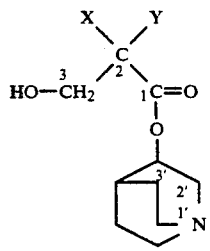

(I)

or a pharmaceutically acceptable salt thereof, wherein X is either (a) a phenyl group optionally substituted by 1 or 2 substituents each independently selected from halo, $CF_3$, $C_1$-$C_4$ alkyl, $C_1$-$C_4$ alkoxy and hydroxy or (b) a thienyl group; and Y is a 5-membered nitrogen-containing heterocyclic group attached to the adjacent carbon atom either by a carbon or a ring nitrogen atom and which is selected from imidazolyl, pyrazolyl, triazolyl and tetrazolyl, Y being optionally substituted by 1 or 2 substituents each independently selected from halo, $CF_3$, $C_1$-$C_4$ alkoxy, hydroxy and amino.

"Halo" means F, Cl, Br or I. $C_3$ and $C_4$ alkyl and alkoxy groups can be straight or branched chain.

X is preferably either (a) a phenyl group optionally substituted by 1 or 2 fluoro atoms or (b) a 3-thienyl group. X is most preferably an unsubstituted phenyl group.

Y is preferably aan unsubstituted heterocyclic group as defined above. Y is more preferably 1H-imidazol-1-yl, 1H-1,2,3-triazol-1-yl, 1H-1,2,4-triazol-1-yl, 1H-pyrazol-1-yl, 1H-tetrazol-1-yl, 1H-imidazol-4(5)-yl, 1H-pyrazol-4-yl, or 1H-pyrazol-3(5)-yl. Y is most preferably 1H-imidazol-1-yl.

Those skilled in the art will appreciate that there are two asymmetric centres in the compounds (I), namely those at the positions identified as 2- and 3'- in FIG. (I). All diastereoisomers whether separated or not are within the scope of this invention. The preferred esters are however the 3R-quinuclidinyl esters. Also, the preferred stereochemistry at position 2 is R. Thus the preferred compounds are (2R,3'R) 3-quinuclidinyl propanoates, and can be represented as follows:

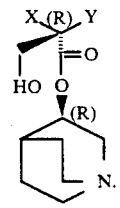

(IA)

A particularly preferred individual compound of the invention is (2R,3'R)-3-quinuclidinyl-3-hydroxy-2-(1H-imidazol-1-yl)-2-phenylpropanoate.

The compounds of the formula (I) can be prepared by the reaction of an ester of the formula (II) with a strong base such as lithium or potassium diisopropylamide, potassium t-butoxide or sodium hydride to form a carbanion, followed by reaction of the carbanion with formaldehyde. The formaldehyde is generally provided either as formaldehyde gas, or as paraformaldehyde (which breaks down to formaldehyde in solution).

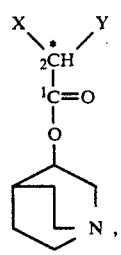

(II)

DETAILED DESCRIPTION

The preferred techniques are as follows.

In one technique, the ester (II) is reacted for a few hours with lithium diisopropylamide in tetrahydrofuran at about −78° C. The reaction mixture is then slowly allowed to warm to room temperature during which time formaldehyde gas, generated e.g. by heating paraformaldehyde, is intermittently passed into the solution.

In another technique, sodium hydride, the ester (II) and paraformaldehyde are reacted together in tetrahydrofuran at about room temperature.

Compounds (I) having R stereochemistry at position 3' are preferred, and these are best obtained by starting with an ester (II) having R stereochemistry at position 3' in formula (II). Likewise the 3S quinuclidinyl esters can be prepared from esters (II) having S stereochemistry at the 3'-position.

It is usually most convenient to start with the 2 RS forms of the esters (II) even is the 2R or 2S, rather than 2RS, end products are required. This will result in a mixture of diastereomers of the compounds (I), and, if desired, these can be separated into the 2R and 2S forms by conventional techniques such as fractional crystallisation (as illustrated in Example 1) or chromatography (as illustrated in Examples 2 and 5). As stated above, in general, the (2R,3'R) forms of the compounds (I) are preferred.

The novel esters (II) also form a part of the invention. The starting materials (II) are obtainable by conventional techniques such as the following:

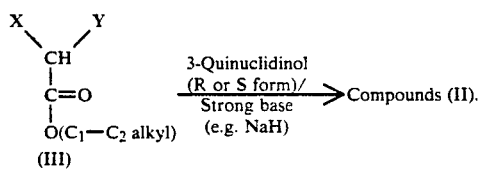

The reaction is typically carried out by heating the reactants in an organic solvent such as toluene at reflux. The compound (III) is most conveniently used in the RS form, and preferably as the methyl ester.

The starting materials (III) also form a part of the invention.

The starting materials (III) are also readily available by conventional techniques. When the heterocycle Y is attached to the adjacent carbon atom by a nitrogen atom, then the following technique is preferred:

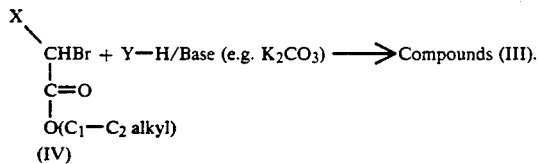

Many of the bromo-compounds (IV) are known and the preparation of any novel bromo-compounds can be carried out conventionally as is illustrated, for example, in Preparations 23–26.

When the heterocycle Y is attached to the adjacent carbon atom by a ring carbon atom, then the compounds (III) can, for example, be prepared as follows:

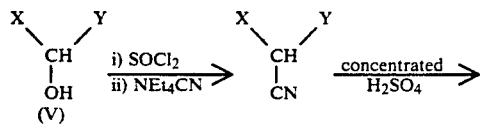

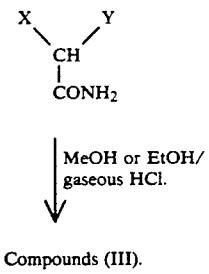

Compounds (III).

Many of the compounds (V) are known and others can be prepared conventionally (see e.g. Preparation 33).

The selectivity of the compounds as muscarinic receptor antagonists can be measured as follows.

Male guinea pigs are sacrificed and the ileum, trachea, bladder and right atrium are removed and suspended in Krebs solution under a resting tension of 1 g at 30° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating double atria is derived from isometrically recorded contractions.

Dose-response curves to carbachol are determined using a 1–5 minute contact time for each dose of agonist until the maximum response is achieved. The organ bath is drained and refilled with Krebs solution containing the lowest dose of the test compound. The test compound is allowed to equilibrate with the tissue for 20 minutes and the agonist dose-response curve is repeated until the maximum response is obtained. The organ bath is drained and refilled with Krebs solution containing the second concentration of test compound and the above procedure is repeated. Typically three concentrations of the test compound are evaluated on each tissue.

The negative log of the molar concentration ($pA_2$) of the test compound which causes a doubling of the agonist concentration to produce the original response is determined by Schild analysis (Arunlakshana and Schild (1959), Brit. J. Pharmacol., 14, 48–58). Using the above pharmacological techniques, tissue selectivity for muscarinic receptor antagonists is determined.

Activity against agonist-induced or nerve-evoked bronchoconstriction of gut or bladder contractility in comparison with changes in heart rate is determined in the anaesthetised dog, cat or guinea pig. Oral activity is assessed in the conscious dog determining compound effects on, lung function, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

The selectivity of the compounds for pulmonary post-junctional as against pre-junctional muscarinic receptors in anaesthetised guinea pigs and cats can be assessed by the following techniques. Acetylcholine released by nerve stimulation activates post-junctional M3 muscarinic receptors to cause contraction of airway smooth muscle and, in addition, activates pre-junctional autoreceptors which inhibit further transmitter release.

Animal studies indicate that these pulmonary pre-junctional muscarinic autoreceptors are of the M2 subtype (Barnes et al, 1989). Non-selective agents like ipratropium bromide will inhibit both sites, resulting, in the case of nerve-mediated responses, in an increase in transmitter release which can overcome the post-junctional receptor blockade. Published literature has shown that ipratropium bromide can actually potentiate vagally-induced bronchoconstriction in anaesthetised guinea pigs (Fryer and Maclagan, Eur. Jou. Pharmacol., 139, 187-191 (1987)). Thus, the effects of the test compounds on pre- and post- junctional muscarinic sites can be determined in vivo by comparing the effect on nerve mediated responses with the effect on responses to exogenously administered acetylcholine.

For example, the compound of Example 1 has been found to antagonise both acetylcholine-induced, and vagally-induced, bronchoconstriction in anaesthetised guinea pigs over the same dose range. This constrasts with ipratropium bromide which is significantly less potent against vagally-induced than against acetylcholine-induced bronchoconstriction. Additionally, at doses below 1 μg/kg of ipratropium bromide, vagally-induced bronchoconstriction is actually potentiated, confirming its pre-junctional effects.

Similar results were obtained from the compound of Example 1 in the anaesthetised cat. The animals were pretreated with propranolol because high sympathetic tone under chloralose anaesthesia may oppose potentiation of vagus nerve-induced bronchoconstriction. The test results indicate that, in addition to its high potency, the compound of Example 1, in contrast to ipratropium bromide, does not interrupt negative feedback control of transmitter release in both guinea-pig and cat. This confirms the demonstrated in vitro selectivity of this compound for M3 as opposed to M2 muscarinic receptors.

As a result of this selectivity for post- as opposed to pre-junctional muscarinic receptors, the compounds of the invention should be more effective bronchodilators in respiratory disease compared to ipratropium bromide.

The acid addition salts of the compounds of formula (I) can be prepared in a conventional manner by treating a solution or suspension of the free base of (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, ascorbic, benzoic, cinnamic, fumaric, sulfuric, phosphoric, hydrochloric, hydrobromic, hydroiodic, sulfamic, sulfonic such as methanesulfonic, benzensulfonic, and related acids.

For treatment of the various conditions described above the compounds of formula (I) may be administered to a subject in need of treatment by a variety of conventional routes of administration, including oral administration, and in an aerosol or dry powder composition for administration by inhalation. The compounds have potential for absorption through the gastro-intestinal tract and thus administration by slow release formulations is also possible.

In general, a therapeutically-effective oral dose for the active compounds of formula (I) is likely to range from 0.01 to 1 mg/kg body weight of the subject to be treated, preferably 0.1 to 0.5 mg/kg. In practice the physician will determine the actual dosage which will be most suitable for an individual patient and it will vary with the age, weight and response of the particular patient. The above dosages are exemplary of the average case but there can, or course, be individual instances where higher or lower dosage ranges are merited, and such are within the scope of this invention.

Although the compounds of formula (I) can be administered alone, they will generally be administered in admixture with a pharmaceutical carrier selected with regard to the intended route of administration and standard pharmaceutical practice. For example, oral administration may be in the form of tablets containing such excipients as starch or lactose, in capsules either alone or in admixture with excipients, in aerosol or dry powder inhaler form, or in the form of elixirs or suspensions containing flavouring or colouring agents.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament.

The invention further includes the use of a compound of the formula (I), or of a pharmaceutically acceptable salt thereof, for the manufacture of a medicament for the treatment of chronic obstructive airways disease or asthma.

The following examples illustrate the preparation of the compounds (I):

EXAMPLE 1 a) (2R,3'R) 3-Quinuclidinyl 3-hydroxy-2-(1H-imidazol-1-yl)-2-phenylpropanoate monohydrate

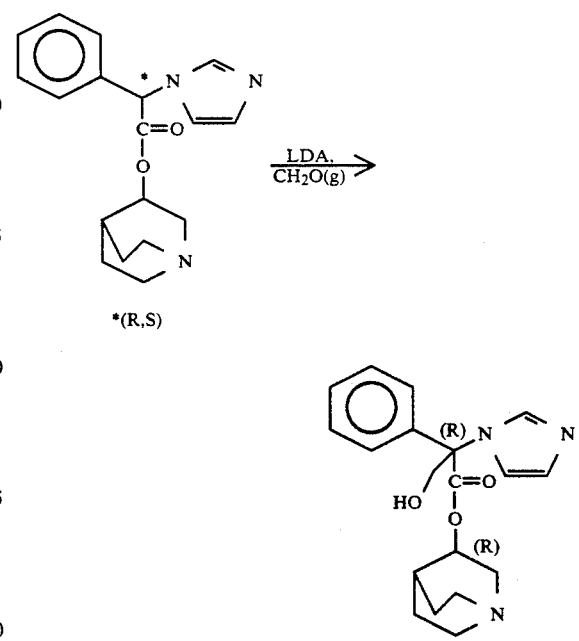

Lithium diisopropylamide (LDA) in tetrahydrofuran (361 ml of a 1.5M solution) was added to a solution of (2RS,3'R) 3-quinuclidinyl 2-(1H-imidazol-1-yl)phenylacetate (see Preparation 1) (152.9 g) in tetrahydrofuran (3.5 liters) at −78° C. After 2 hours the reaction was allowed to slowly reach room temperature during which time formaldehyde gas (generated by heating paraformaldehyde (39 g) in a stream of nitrogen) was intermittently added. Saturated aqueous ammonium chloride was then added and the organic layer was subsequently extracted with further ammonium chloride solution (5×250 ml) and then with 1M hydrochloric acid (2×250 ml). The combined aqueous extracts were extracted with ethyl acetate, basified with solid potassium carbonate and exhaustively extracted with further ethyl acetate. The organic extracts, before and after basifying, were separately dried over magnesium sulphate, evaporated under reduced pressure, and crystallised from acetone. The combined solids were recrystallised from acetone to give (2R, 3'R) 3-quinuclidinyl 3-hydroxy-2-(1H-imidazol-1-yl)-2-phenylpropanoate as an acetone solvate (38.6 g, 44.3% based on a single isomer). A portion of this (10 g) was dissolved in methanol (100 ml), filtered, evaporated to dryness under reduced pressure and dissolved in cold 0.1M hydrochloric acid (305 ml). Addition of 0.1M sodium hydroxide (305 ml) then gave the title compound as a white solid, (6.9 g, 68%), m.p. 90°-91° C., $[\alpha]_{589}^{25}+7.6°$ (c=1% in ethanol).

Analysis %: Found: C,63,53; H,7.06; N,11.73. $C_{19}H_{23}N_3O_3.H_2O$ requires: C,63.49; H,7.01; N,11.69.

b) (2S,3'R) 3-Quinuclidinyl 3-hydroxy-2-(1H-imidazol-1-yl)-2-phenylpropanoate hemihydrate Concentration of the acetone mother liquors from part (a) gave, on slow crystallisation, the 2S title compound as a white solid, m.p. 143°-145° C. $[\alpha]_{589}^{25}-8.8°$ (c=1% in ethanol).

Analysis %: Found: C,65.06; H,6.76; N,11.69. $C_{19}H_{23}N_3O_3.\frac{1}{2} H_2O$ requires: C,65.12; H,6.90; N,11.99.

EXAMPLE 2

(2R,3'R) and (2S,3'R) 3-Quinuclidinyl 3-hydroxy-2-phenyl-2-(1H-1,2,4-triazol-1-yl)propanoate dihydrochlorides

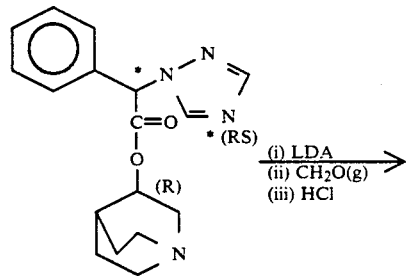

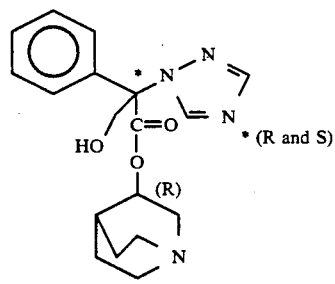

Lithium diisopropylamide (13.77 ml of a 1.5M solution in tetrahydrofuran) was added to a solution of (2RS,3'R) 3-quinuclidinyl 2-phenyl-2-(1H-1,2,4-triazol-1-yl)acetate (see Preparation 2) (5.86 g) in tetrahydrofuran (100 ml) at −78° C. After 2 hours the reaction was allowed to slowly reach room temperature during which time formaldehyde gas [generated by heating paraformaldehyde (10 g) in a stream of nitrogen] was intermittently added. Saturated aqueous ammonium chloride was then added, the tetrahydrofuran evaporated and the aqueous residue partitioned between 10% aqueous potassium carbonate and ethyl acetate. The organic layer was dried over magnesium sulphate and evaporated under reduced pressure to give a crude product that was purified by chromatography on silica gel, performing a gradient elution using dichloromethane plus methanol (2→10%) as eluant. Evaporation of appropriate fractions gave a residue (330 mg) which was further purified by chromatography on silica gel eluting with ethyl acetate/ether/diethylamine/methanol (50:50:5:5) to give, after evaporation of appropriate fractions and treatment with ethereal hydrogen chloride, the two title compounds as white amorphous solids.

Diastereoisomer I (higher Rf by tlc) (110 mg, 2.8%): $^1$H-N.M.R. (300 MHz, CDCl$_3$), $\delta$=1.2–1.8 (m, 4H); 2.1 (m, 1H); 2.6–2.9 (m, 5H); 3.25 (m, 1H); 4.4–4.7 (m, 2H); 5.0 (m, 1H); 7.2–7.5 (m, 5H); 7.98 (s, 1H); 8.07 (s, 1H) ppm.

Mass spectrum: m/e (M+)=342.

Diastereoisomer II (lower Rf by tlc) (150 mg, 3.8%): $^1$H-N.M.R. (300 MHz, CDCl$_3$), $\delta$=1.2–1.8 (m, 4H); 2.1 (m, 1H); 2.6–2.9 (m, 5H); 3.25 (m, 1H); 4.4–4.7 (m, 2H); 5.0 (m, 1H); 7.2–7.5 (m, 5H); 7.98 (s, 1H); 8.07 (s, 1H) ppm.

Mass spectrum: m/e (M+)=342.

Which diastereoisomer had 2R stereochemistry, and which 2S, was not elucidated.

EXAMPLE 3

(2R,3'R) and (2S,3'R) 3-Quinuclidinyl 3-hydroxy-2-phenyl-2-(1H-1,2,3-triazol-1-yl) propanoate dihydrochlorides

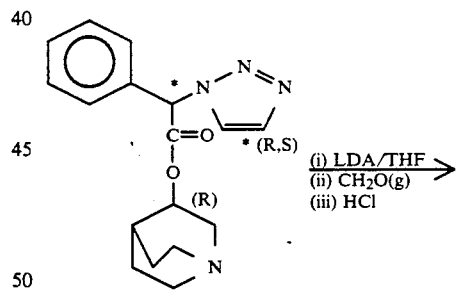

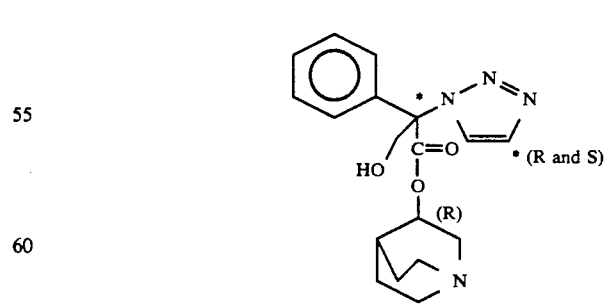

(2RS,3'R) 3-quinuclidinyl 2-phenyl-2-(1H-1,2,3-triazol-1-yl)acetate (see Preparation 3) (2.1 g) in tetrahydrofuran (60 ml) was treated as described in Example 2 with lithium diisopropylamide (5.15 ml of a 1.5M solution in tetrahydrofuran) and formaldehyde gas (4 g). The crude product was purified by chromatography on silica gel, eluting with ethyl acetate/ether/diethylamine/methanol (50:50:5:5), to give, after evaporation of appropriate fractions and treatment with ethereal hydrogen chloride, the two title compounds as amorphous white solids. Which diastereoisomer had 2R stereochemistry, and which 2S, was not elucidated.

Diastereoisomer I (higher Rf by tlc) (155 mg, 11.2%):
$^1$H-N.M.R. (300 MHz, CDCl$_3$) δ=1.2–1.8 (m, 4H); 2.1 (m, 1H); 2.6–3.0 (m, 5H); 3.3 (m, 1H); 4.5–4.9 (m, 2H); 5.1 (m, 1H); 7.2–7.5 (m, 6H); 7.8 (s, 1H) ppm.

Mass spectrum: m/e (M+)=342.

Diastereoisomer II (lower Rf by tlc) (80 mg 5.8%):
$^1$H-N.M.R. (300 MHz, CDCl$_3$), δ=1.2–1.8 (m, 4H); 2.1 (m, 1H); 2.6–3.0 (m, 5H); 3.3 (m, 1H); 4.5–4.9 (m, 2H); 5.1 (m, 1H); 7.2–7.5 (m, 6H); 7.8 (s, 1H) ppm.

Mass spectrum: m/e (M+)=342.

EXAMPLE 4

(2RS,3'R) 3-Quinuclidinyl 3-hydroxy-2-phenyl-2-(1H-pyrazol-1-yl)propanoate dihydrochloride

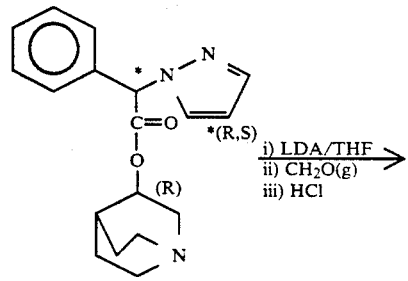

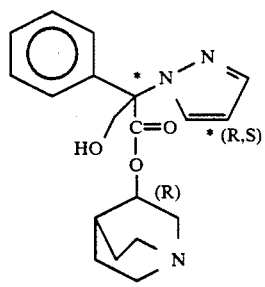

(2RS,3R) 3-quinuclidinyl 2-phenyl-2-(1H-pyrazol-1-yl)acetate (see Preparation 4) (1.18 g) in tetrahydrofuran (30 ml), treated as described in Example 2 with lithium diisopropylamide (3.03 ml of a 1.5M solution in tetrahydrofuran) and formaldehyde gas (2.4 g), gave a crude product which, when treated directly with ethereal hydrogen chloride, gave the title compound, a mixture of diastereoisomers, as an amorphous white solid (1.33 g, 85%).

$^1$H-N.M.R. (300 MHz, CDCl$_3$), δ=1.2–1.8 (m, 4H); 2.1 (m, 1H); 2.6–3.0 (m, 5H); 3.25 (m, 1H); 4.4–4.8 (m, 2H); 5.1 (m, 1H); 6.3 (s, 1H); 7.15 (s, 1H); 7.2–7.5 (m, 5H); 7.65 (s, 1H) ppm.

Mass spectrum: m/e (M+)=341.

EXAMPLE 5

(2R,3R) and (2S,3R) 3-Quinuclidinyl 3-hydroxy-2-pheny-2-(1H-tetrazol-1-yl)propanoate

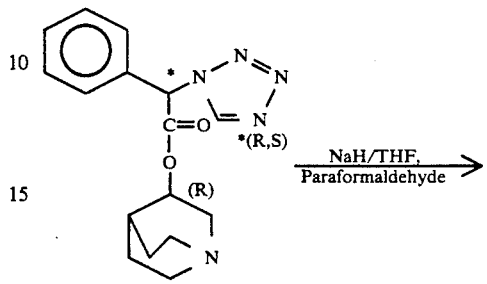

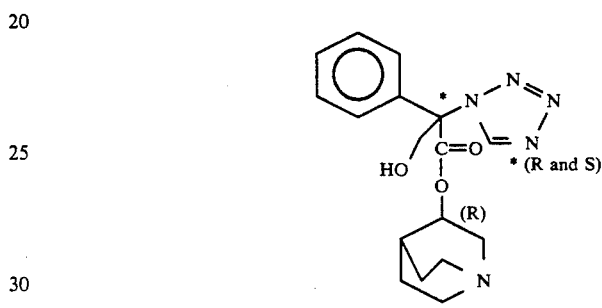

Sodium hydride (23 mg of an 80% dispersion in oil) was added to a mixture of (2RS,3R) 3-quinuclidinyl 2-phenyl-2-(1H-tetrazol-1-yl)acetate (see Preparation 5) (0.7 g) and paraformaldehyde (87 mg) in tetrahydrofuran (20 ml) at room temperature. After ½ hour saturated aqueous ammonium chloride was added, the tetrahydrofuran was evaporated under reduced pressure, and the aqueous residue extracted with ethyl acetate. The organic layer was dried over magnesium sulphate and evaporated under reduced pressure to leave a residue which was purified by chromatography on silica gel performing a gradient elution using dichloromethane pluse methanol 2→10% as eluant. Evaporation of appropriate fractions gave the two title compounds. Which isomer had 2R stereochemistry, and which 2S, was not assessed.

Diastereoisomer I (higher Rf by tlc) as a yellow oil (21 mg, 5.4%):

$^1$H-N.M.R. (300 MHz, CDCl$_3$) δ=1.2–1.8 (m, 4H); 2.1 (m, 1H); 2.6–3.0 (m, 5H); 3.3 (m, 1H); 4.7 (m, 2H); 5.05 (m, 1H); 7.2–7.6 (m, 5H); 8.9 (s, 1H) ppm.

Mass spectrum: m/e (M+)=343.

Diastereoisomer II (lower Rf by tlc) as a waxy yellow solid (10 mg, 2.5%):

$^1$H-N.M.R. (300 MHz, CDCl$_3$) δ=1.2–1.8 (m, 4H); 2.05 (m, 1H); 2.6–2.9 (m, 5H); 3.2 (m, 1H); 4.7 (m, 2H); 5.1 (m, 1H); 7.2–7.6 (m, 5H); 8.85 (s, 1H) ppm.

Mass spectrum: m/e (M+)=343.

EXAMPLE 6

(2R,3R) and (2S,3R) 3-Quinuclidinyl 3-hydroxy-2-(1H-imidazol-1-yl)-2-(thien-3-yl)propanoate dihydrochloride

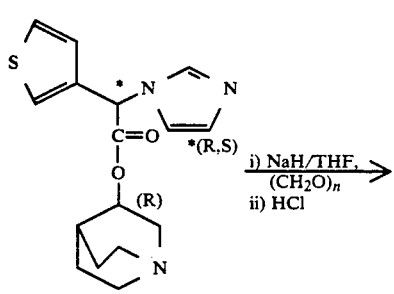

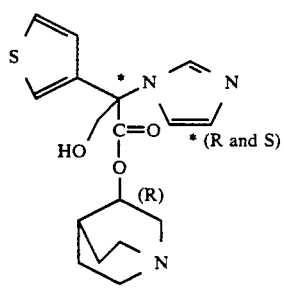

(2R,3R) 3-Quinuclidinyl 2-(1H-imidazol-1-yl)-2-(thien-3-yl)acetate (see Preparation 6) (1.0 g) and paraformaldehyde (0.12 g) in tetrahydrofuran (20 ml) were treated as described in Example 5 with sodium hydride (31 mg) giving a crude product which was purified by chromatography on silica gel using ethyl acetate/ether/methanol/diethylamine (50:50:10:5) as eluant. Evaporation of appropriate fractions and treatment with etheral hydrogen chloride gave the two title compounds, of uncharacterised stereochemistry, as amorphous white solids.

Diastereoisomer I (higher Rf by tlc) (220 mg, 33%):

$^1$H-N.M.R. (300 MHz, CDCl$_3$) δ=0.8–1.8 (m, 4H); 2.0 (m, 1H); 2.4–2.8 (m, 5H); 3.25 (m, 1H); 4.3–4.6 (m, 2H); 4.95 (m, 1H); 7.0–7.8 (m, 6H).

Mass spectrum: m/e (M+)=347.

Diastereoisomer II (lower Rf by tlc) (180 mg, 27%):

$^1$H-N.M.R. (300 MHz, CDCl$_3$) δ=0.8–1.8 (m, 4H); 2.0 (m, 1H); 2.6–2.8 (m, 5H); 3.2 (m, 1H); 4.3–4.6 (m, 2H); 5.0 (m, 1H); 7.0 (m, 3H); 7.4 (m, 2H); 7.7 (s, 1H).

Mass spectrum: m/e (M+)=347.

EXAMPLE 7

(2R,3R) 3-Quinuclidinyl 2-(4-fluorophenyl)-3-hydroxy-2-(1H-imidazol-1-yl)propanoate dihydrochloride

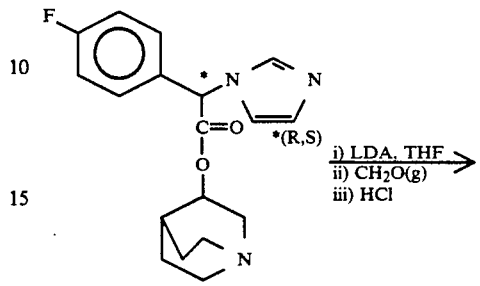

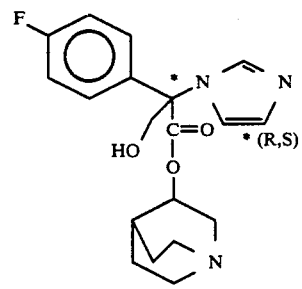

(2RS,3R) 3-quinuclidinyl 2-(4-fluorophenyl)-2-(1H-imidazol-1-yl)acetate (see Preparation 7) (0.73 g) in tetrahydrofuran (25 ml) treated, as described in Example 2, with lithium diisopropylamide (1.62 ml of a 1.5M solution in tetrahydrofuran and formaldehyde gas (1.4 g) gave a crude product which was purified by chromatography on silica gel, performing a gradient elution with dichloromethane containing methanol (0→10%) and concentrated ammonia (0→1%). Evaporation of appropriate fractions and treatment with ethereal hydrogen chloride gave the title compound, a mixture of diastereoisomers, as a white amorphous solid (0.59 g, 61%).

$^1$H-N.M.R. (300 MHz, CDCl$_3$) δ=0.8–2.2 (m, 5H); 2.6–3.6 (m, 6H); 4.2–4.6 (m, 2H); 5.0 (m, 1H); 7.0–7.8 (m, 7H) ppm.

Mass spectrum: m/e (M+)=359.

EXAMPLE 8

(2RS,3R) 3-Quinuclidinyl 2-(2-fluorophenyl)-3-hydroxy-2-(1H-imidazol-1-yl)propanoate dihydrochloride

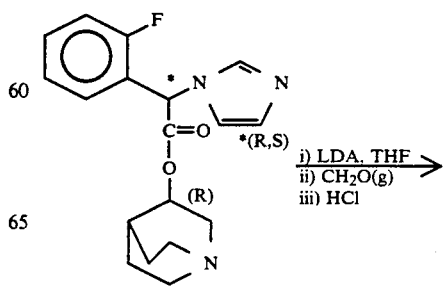

-continued

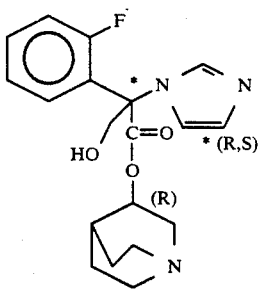

The title compound was obtained from (2RS,3R) 3-quinuclidinyl 2-(2-fluorophenyl)-2-(1H-imidazol-1-yl)acetate (see Preparation 8) (0.96 g), lithium diisopropylamide and formaldehyde gas, by the method described in Example 7, as a white amorphous solid (0.51 g, 40.5%).

¹H-N.M.R. (300 MHz, CDCl₃) δ=1.2-1.8 (m, 4H); 2.0 (m, 1H); 2.5-3.0 (m, 5H); 3.25 (m, 1H); 4.3 (m, 2H); 5.0 (m, 1H); 6.8-7.3 (m, 6H); 7.9 (s, 1H) ppm.

Mass spectrum: m/e (M+)=359.

(2RS,3'R) 3-Quinuclidinyl 3-hydroxy-2-(1H-imidazol-4(5)-yl)-2-phenylpropanoate dihydrochloride

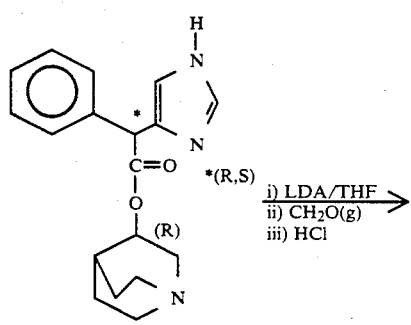

(2RS,3'R) 3-Quinuclidinyl 2-phenyl-2-(1H-imidazol-4(5)-yl)acetate (see Preparation 9) (0.52 g) in tetrahydrofuran (15 ml) treated, as described in Example 2, with lithium diisopropylamide (2.45 ml of a 1.5M solution in tetrahydrofuran) and formaldehyde gas (1 g), gave a crude product which was purified by chromatography on silica gel performing a gradient elution using dichloromethane/concentrated ammonia (80:1) plus 5→20% methanol as eluant. Evaporation of appropriate fractions and treatment with ethereal hydrogen chloride gave the title compounds, a mixture of diastereoisomers, as an amorphous white solid (173 mg, 23%).

¹H-N.M.R. (300 MHz, DMSO-D₆) δ=1.4-2.3 (m, 5H); 3-3.3 (m, 5H); 3.6 (m, 1H); 4.2-4.5 (m, 2H); 5.1 (m, 1H); 7.2-7.6 (m, 6H); 9.1 (s, 1H) ppm.

Mass spectrum: m/e (M+)=341.

EXAMPLE 10

(2RS,3'R) 3-Quinuclidinyl 3-hydroxy-2-phenyl-2-(1H-pyrazol-4-yl)propanoate dihydrochloride

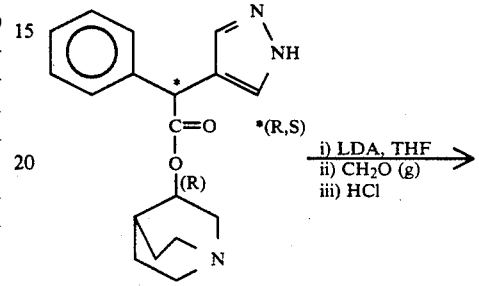

This was obtained by a similar method to that described in Example 9 using (2RS,3'R) 3-quinuclidinyl 2-phenyl-2-(1H-pyrazol-4yl)acetate (see Preparation 10) (0.9 g). The title compound, a mixture of diastereoisomers, was obtained as an amorphous white solid (290 mg, 24%).

Analysis %: Found: C,55.27; H,6.50; N,9.90. C₁₉H₂₃N₃O₃.2HCl requires: C,55.08; H,6.08; N,10.14.

EXAMPLE 11

(2RS,3'R) 3-Quinuclidinyl 3-hydroxy-2-phenyl-2-(1H-pyrazol-3(5)-yl)propanoate dihydrochloride

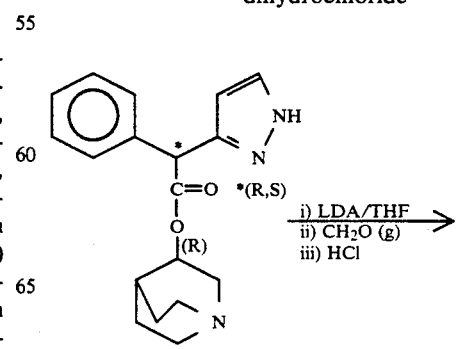

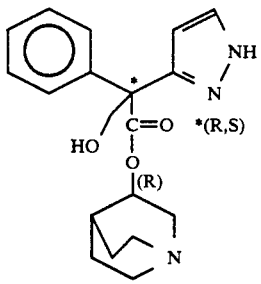

This was obtained by a similar method to that described in Example 9 using (2RS,3'R) 3-quinuclindinyl 2-phenyl-2-(1H-pyrazol-3(5)-yl)acetate (see Preparation 11) (0.71 g). The title compound, a mixture of diastereoisomers, was obtained as an amorphous white solid (500 mg, 53%).

Analysis %: Found): C,53.53; H,6.03; N,9.46. $C_{19}H_{23}N_3O_3 \cdot 2HCl \cdot \frac{1}{2} H_2O$ requires: C,53.91; H,6.19; N,9.92.

The following Preparations illustrate the preparation of the novel starting materials used in the preceding Examples:

PREPARATION 1

(2RS,3'R) 3-quinuclidinyl 2-(1H-imidazol-1-yl)phenylacetate

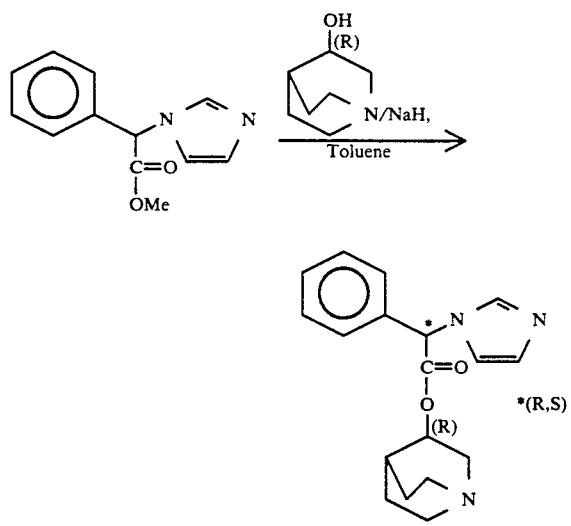

Sodium hydride (4.6 g as an 80% dispersion in oil), after washing with toluene, was added to (R)-3-quinuclidinol (100.8 g) (prepared as described by Ringdahl et. al. in Acta. Pharm. Suec., 281, 16, 1979) and (RS) methyl 2-imidazol-1-yl)phenylacetate (see Preparation 12) (132 g) in toluene (2.5 liters). The mixture was refluxed for two hours with continuous removal of distillate with, when necessary, the addition of fresh toluene. Saturated brine was added, the toluene decanted off, and the aqueous residue partitioned between further brine and ethyl acetate. The ethyl acetate and toluene extracts were separately dried over magnesium sulphate, evaporated under reduced pressure and the residues combined to give the title compound as an orange oil (152.2 g, 82%).

$^1$H-N.M.R. (300 MHz, CDCl$_3$) δ=1.2–1.8 (m, 4H); 2.0 (m, 1H); 2.75 (m, 5H); 3.3 (m,1H); 5.0 (m, 1H); 5.95 (s, 1H); 7.25 (s, 1H); 7.3 (s, 1H); 7.4 (m, 5H); 7.6 (s, 1H) ppm.

Mass spectrum: m/e (M+)=311.

PREPARATIONS 2 TO 11

The following tabulated Preparations of the general formula:

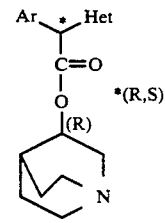

were obtained as oils by similar methods to that described for Preparation 1 using (R) -3-quinuclidinol and the appropriate methyl ester in toluene with sodium hydride as the catalyst. The exchangeable heterocyclic proton in Preparations 9, 10 and 11 necessitated the use of an extra equivalent of sodium hydride. In Preparation 10, the compound was converted to the dihydrochloride using hydrogen chloride gas in ether as the last step. Purification, where necessary, was by chromatography by gradient elution on silica gel using the solvents indicated.

| Preparation No. | Ar | Het | Chromatography solvent | Analytical data |
|---|---|---|---|---|
| 2 | ![phenyl] | ![imidazole] | CH$_2$Cl$_2$ + 0→4% MeOH | $^1$H-N.M.R.(300MHz, CDCl$_3$)δ= 1.2–1.8(m, 4H); 2.1(m, 1H); 2.6–3.0(m, 5H); 3.25(m, 1H); 4.95 (m, 1H); 6.2(s, 1H); 7.5(s, 5H); 8.0(s, 1H); 8.15(s, 1H)ppm. Mass spectrum: m/e (M+)=312 |
| 3 | ![phenyl] | ![pyrazole] | CH$_2$Cl$_2$ + 2→10% MeOH | $^1$H-N.M.R.(300MHz, CDCl$_3$)δ= 1.4–2.0(m, 4H); 2.2(m, 1H); 2.8–3.4(m, 5H); 3.5(m, 1H); 5.2 (m, 1H); 6.4(s, 1H); 7.0–7.8(m, 7) ppm. Mass spectrum: m/e(M+)=312 |

-continued

| Preparation No. | Ar | Het | Chromatography solvent | Analytical data |
|---|---|---|---|---|
| 4 | phenyl | 1-methylpyrazol-5-yl | $CH_2Cl_2$ + 2→10% MeOH | $^1$H-N.M.R.(300MHz, $CDCl_3$)δ= 1.2–1.8(m, 4H); 2.0(m, 1H); 2.6–2.9(m, 5H); 3.2(m, 1H); 4.85 (m, 1H); 5.2(s, 1H); 6.3(s, 1H); 7.2–7.5(m, 5H); 7.55(s, 2H)ppm. Mass spectrum m/e(M+)=311 |
| 5 | phenyl | 1-methyl-1,2,4-triazol-5-yl | No chromatography | $^1$H-N.M.R.(300MHz, $CDCl_3$)δ= 1.2–1.8(m, 4H); 2.1(m, 1H); 2.6–3.0(m, 5H); 3.3(m, 1H); 5.05 (m, 1H); 6.2(s, 1H); 7.2–7.6(m, 5H); 8.9(s, 1H)ppm. |
| 6 | 3-thienyl | 1-methylimidazol-5-yl | No chromatography | $^1$H-N.M.R.(300MHz, $CDCl_3$)δ= 1.2–1.8(m, 4H); 2.0(m, 1H); 2.6–3.0(m, 5H); 3.3(m, 1H); 4.95 (m, 1H); 6.05(s, 1H); 7.0–7.8(m, 6H)ppm. Mass spectrum: m/e(M+)=318 |
| 7 | 4-fluorophenyl | 1-methylimidazol-5-yl | $CH_2Cl_2$ + 0→15% MeOH | $^1$H-N.M.R.(300MHz, $CDCl_3$)δ= 0.8–1.6(m, 4H); 2.1(m, 1H); 2.6–3.0(m, 5H); 3.2(m, 1H); 4.95 (m, 1H); 5.95(s, 1H); 7.0–7.8(m, 7H)ppm. Mass spectrum m/e(M+)=329 |
| 8 | 2-fluorophenyl | 1-methylimidazol-5-yl | $CH_2Cl_2$ + 0→15% MeOH | $^1$H-N.M.R.(300MHz, $CDCl_3$)δ= 1.2–1.9(m, 4H); 2.0(m, 1H); 2.5–2.9(m, 5H); 3.2(m, 1H); 5.0 (m, 1H); 6.2(s, 1H); 7.0–7.5(m, 6H); 7.06(s, 1H)ppm. Mass spectrum m/e(M+)=329 |
| 9 | phenyl | 5-methylimidazol-4-yl (NH) | — | $^1$H-N.M.R.(300MHz, $CDCl_3$)δ= 1.2–1.8(m, 4H); 2.0(m, 1H); 2.5–2.9(m, 5H); 3.2(m, 1H); 5.0 (m, 1H); 6.3(s, 1H); 6.9(s, 1H); 7.2–7.5(m, 5H); 7.6(s, 1H)ppm. |
| 10 | phenyl | 4-methylpyrazol-3-yl (NH) | — | Analysis %:- Found: C, 55.27; H, 6.50; N, 9.90 $C_{19}H_{23}N_3O_3$·2HCl requires: C, 55.08; H, 6.08; N, 10.14. |
| 11 | phenyl | 3-methylpyrazol-5-yl (NH) | — | $^1$H-N.M.R.(300MHz, $CDCl_3$)δ= 1.2–1.8(m, 4H); 2.0(m, 1H); 2.6–2.8(m, 5H); 3.2(m, 1H); 4.85 (m, 1H); 5.0(s, 1H); 6.3(s, 1H); 7.3(m, 5H); 7.6(s, 2H)ppm. |

PREPARATION 12

(RS) Methyl 2-(imidazol-1-yl)-2-phenylacetate

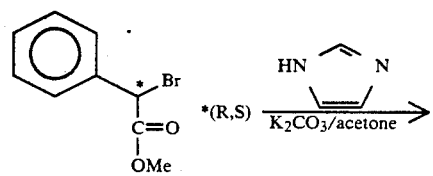

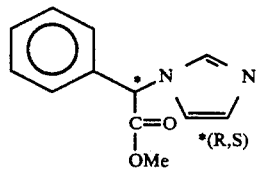

(RS) Methyl 2-bromo-2-phenylacetate (171.75 g), imidazole (102 g) and potassium carbonate (227.7 g) were stirred in acetone (1.75 liters for 60 hours. After settling, the supernatant was decanted off and the residue washed thoroughly with acetone. The acetone was evaporated under reduced pressure and the residue in ethyl acetate was washed with water and extracted twice with 2M hydrochloric acid. The combined acid extracts, after washing once with ether, were basified with solid potassium carbonate and extracted with toluene containing 10% ethyl acetate. The organic extracts were dried over magnesium sulphate and evaporated under reduced pressure to give the title compound as a yellow oil (132 g, 81%).

$^1$H-N.M.R. (300 MHz, CDCl$_3$) δ=3.85 (s, 3H); 5.95 (s, 1H); 7.05 (s, 1H); 7.1 (s, 1H); 7.2–7.5 (m, 5H); 7.6 (s, 1H) ppm.

PREPARATION 13

(RS) Methyl 2-phenyl-2-(1H-1,2,4-triazol-1-yl)acetate

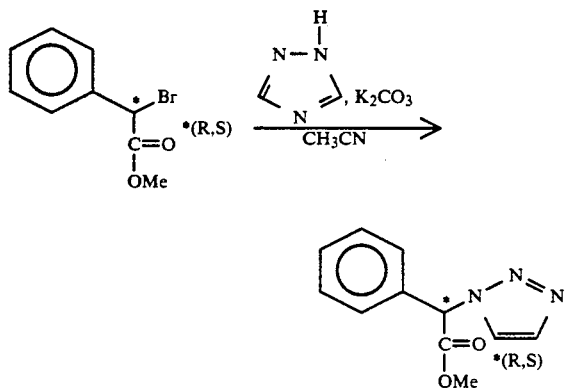

A mixture of (RS) methyl 2-bromo-2-phenylacetate (25 g), 1,2,4-triazole (8.28 g) and potassium carbonate (16.5 g) in acetonitrile (200 ml) was refluxed for 3 hours, cooled evaporated under reduced pressure and the residue partitioned between ethyl acetate and 10% potassium carbonate solution. The organic extracts were washed with water, extracted twice with 2M hydrochloric acid and the combined acid extracts, after washing once with ether, were basified with solid potassium carbonate and extracted with ethyl acetate. The organic extracts were dried over magnesium sulphate and evaporated under reduced pressure to give the title compound as a yellow oil (10.2 g, 43%).

$^1$H-N.M.R. (300 MHz, CDCl$_3$) δ=3.85 (s, 3H); 6.2 (s, 1H); 7.45 (m, 5H); 8.0 (s, 1H); 8.15 (s, 1H) ppm.

PREPARATIONS 14 to 19

The following tabulated Preparations of the general formula:

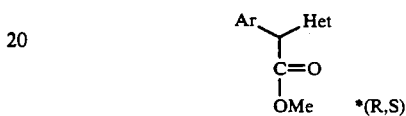

were obtained by similar methods to that described for either Preparation 12 or 13 using the appropriate bromo-ester and heterocycle (H-Het). Individual experimental variations are indicated in the table. Purification, where necessary, was by chromatography on silica gel by gradient elution using the solvents indicated.

| Preparation No. | Ar | H-Het | Experimental method and chromatography solvent | Physical and analytical data |
|---|---|---|---|---|
| 14 | phenyl | imidazole | Method as Preparation 13 | Yellow oil; $^1$H-N.M.R.(300MHz, CDCl$_3$)δ=3.9(s, 3H); 6.7(s, 1H); 7.5(m, 5H); 7.75(s, 2H)ppm. |
| 15 | phenyl | pyrazole | Method as Preparation 13/ no acid extraction | Yellow oil; $^1$H-N.M.R. (300MHz, CDCl$_3$)δ=3.8(s, 3H); 6.25(s, 1H; 6.3(s, 1H); 7.4(m, 6H); 7.6 (s, 1H)ppm. |
| 16 | phenyl | tetrazole | Method as Preparation 12/ no acid extraction | White solid from ether; m.p. 96–98° C.; $^1$H-N.M.R(300MHz, CDCl$_3$)δ= s, 3H); 6.6(s, 1H); 7.5(m, 5H); 8.8(s, 1H)ppm. |
| 17 | thienyl | imidazole | Method as Preparation 12 (without K$_2$CO$_3$)/ no acid extraction, dichloromethane 2 →5% methanol | Yellow oil; $^1$H-N.M.R.(300MHz, CDCl$_3$)δ=3.85(s, 3H); 6.05(s, 1H); 7–7.7(m, 6H)ppm |
| 18 | 4-F-phenyl | imidazole | As Preparation 12 | Yellow oil; $^1$H-N.M.R.(300MHz, CDCl$_3$)δ=3.95(s, 3H); 5.95(s, 1H); 7.05(s, 1H); 7.1(m, 3H); 7.3 (m, 2H); 7.6(s, 1H)ppm. |

| Preparation No. | Ar | H-Het | Experimental method and chromatography solvent | Physical and analytical data |
|---|---|---|---|---|
| 19 | 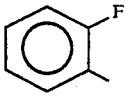 |  | As Preparation 12 | Yellow oil; $^1$H-N.M.R.(300MHz, CDCl$_3$)$\delta$=3.85(s, 3H); 6.2(s, 1H); 6.2(s, 1H); 7.0–7.5(m, 6H); 7.6(s, 1H)ppm. |

PREPARATION 20

(RS) Methyl 2-(1H-Imidazol-4(5)-yl)2-phenylacetate

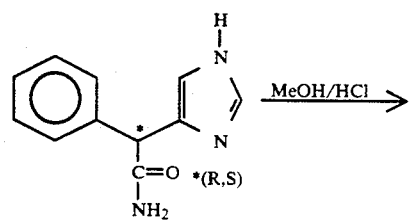

(RS) 2-(1H-imidazol-4(5)-yl)-2-phenylacetamide (see Preparation 27) (1.3 g) in methanol (25 ml) was stirred at reflux under an atmosphere of hydrogen chloride gas for 1.5 hours, evaporated under reduced pressure and partitioned between ethyl acetate and 10% aqueous potassium carbonate solution. The organic layer was dried over magnesium sulphate, evaporated under reduced pressure, and the residue triturated with ether to give the title compound as a white solid (830 mg, 59%) m.p. 96°–98° C.

Analysis %: Found: C66.52; H,5.57; N,12.97. C$_{12}$H$_{12}$N$_2$O$_2$ requires: C,66.65; H,5.59; N,12.96.

PREPARATION 21

(RS) Methyl 2-phenyl-2-(1H-pyrazol-4-yl)acetate

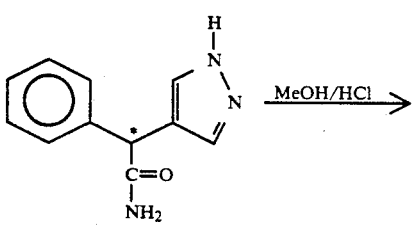

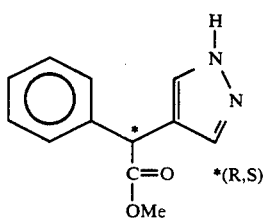

This was obtained by a similar method to that described in Preparation 20 using (RS) 2-phenyl-2-(1H-pyrazol-4-yl)acetamide (see Preparation 28) (1.9 g). The title compound, as a white solid, was obtained by trituration with hexane (1.74 g, 85%), m.p. 100°–103° C.

Analysis %: Found: C,66.54; H,5.63; N,12.90. C$_{12}$H$_{12}$N$_2$O requires: C,66.65; H,5.59; N,12.96.

PREPARATION 22

(RS) Methyl 2-phenyl-2-(1H-pyrazol-3-(5)acetate

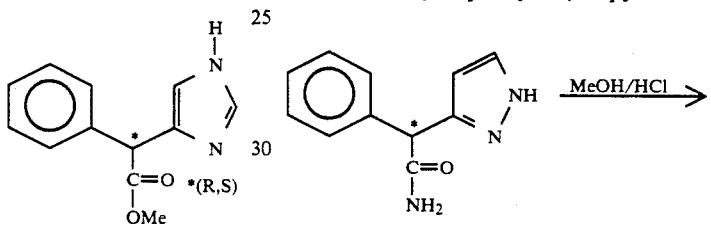

This was obtained by a similar method to that described in Preparation 20 using (RS) 2-phenyl-2-(1H-pyrazol-3(5)-yl)acetamide (see Preparation 29) (2.0 g). The title compound, as a white solid, was obtained by trituration with hexane (1.6 g, 74%), m.p. 83°–85° C.

Analysis %: Found: C,66.60; H,5.59; N,12.95. C$_{12}$H$_{12}$N$_2$O$_2$ requires: C,66.65; H,5.59; N,12.95.

PREPARATION 23

(RS) Methyl 2-bromo-2-(thien-3-yl)acetate

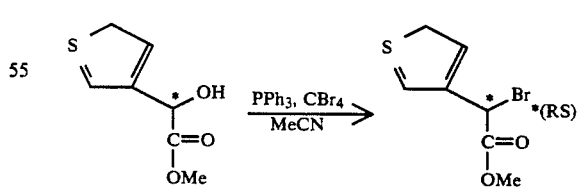

A mixture of (RS) methyl 2-hydroxy-2-(thien-3-yl)acetate (see Preparation 24) (4.49 g), triphenylphosphine (8.21 g) and carbon tetrabromide (10.4 g) in acetonitrile (100 ml) was refluxed for 2 hours, cooled, further triphenylphosphine (2.5 g) and carbon tetrabromide (3 g) were added, and refluxing was continued for a further 2 hours. After cooling, the mixture was used directly, without further purification, in Preparation 17.

PREPARATION 24

(RS) Methyl 2-hydroxy-2-(thien-3-yl)acetate

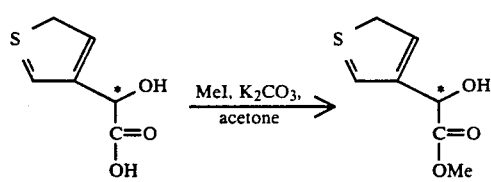

A mixture of (RS) 2-hydroxy-2-(thien-3-yl)acetic acid (prepared as described in Akiv. Kemi., 58, 519, 1957) (6.32 g), methyl iodide (17 g) and potassium carbonate (6 g) in acetone was refluxed for 2 hours, evaporated under reduced pressure and the residue partitioned between ethyl acetate and water. The organic extracts, after drying over magnesium sulphate, were evaported to leave the title compound as a yellow oil (4.49 g, 67%).

1-H-N.M.R. (300 MHz, CDCl$_3$) δ=3.85 (m, 3H); 5.35 (m, 1H); 7.15 (d, 1H); 7.35 (m, 2H) ppm.

PREPARATION 25

(RS) Methyl 2-bromo-2-(4-fluorophenyl)acetate

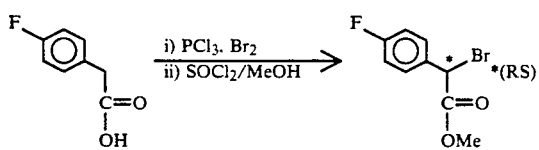

4-Fluorophenylacetic acid (30.6 g), phosphorus trichloride (2 g) and bromine (36 g) in benzene (100 ml) were refluxed for 2 days, cooled, thionyl chloride (47 g) and N,N-dimethylformamide (0.2 g) were then added, the reaction mixture was refluxed for 1 hour, cooled, and methanol (100 ml) added. This mixture was refluxed for ½ hour, cooled, evaporated under reduced pressure and the residue distilled to give the title compound as a clear liquid (35 g, 71%), b.p. 104° C./2 mm.Hg.

$^1$H-N.M.R. (300 MHz, CDCl$_3$) δ=3.8 (3H, s); 5.35 (s, 1H); 7.1 (m, 2H); 7.55 (m, 2H).

PREPARATION 26

(RS) Methyl 2-bromo-2-(2-fluorophenyl)acetate

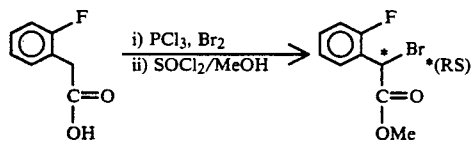

2-Fluorophenylacetic acid (30.6 g), treated as in Preparation 25, gave the title compound as a clear liquid (28 g, 57%), b.p. 90°-92° C./2 mm.Hg.

$^1$H-N.M.R. (300 MHz, CDCl$_3$) δ=3.85 (s, 3H); 5.75 (s, 1H); 7.0-7.8 (m, 4H).

PREPARATION 27

(RS) 2-(1H-Imidazol-4(5)-yl)-2-phenylacetamide

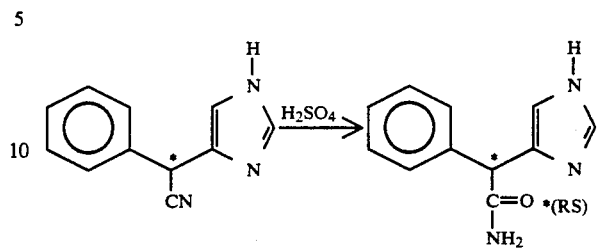

(RS) 2-(1H-Imidazol-4(5)-yl)-2-phenylacetonitrile (see Preparation 30) (1.69 g) in concentrated sulphuric acid (6 ml) was stirred for 18 hours at 0° C., carefully basified with 50% aqueous sodium hydroxide and extracted with ethyl acetate containing 5% methanol. The organic layer was dried over magnesium sulphate, evaporated under reduced pressure, and the residue crystallised from ethyl acetate to give the title compound as a white solid (1.36 g, 73.5%), m.p. 146°-147° C.

Analysis %: Found: C,65.05; H,5.43; N,20.76.
C$_{11}$H$_{11}$N$_3$O requires: C,65.65; H,5.51; N,20.88.

PREPARATION 28

(RS) 2-Phenyl-2-(1H-pyrazol-4-yl)acetamide

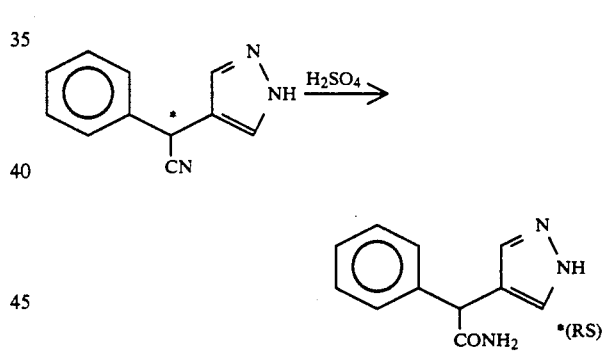

This was obtained by a similar method to that described in Preparation 27 using (RS) 2-phenyl-2-(1H-pyrazol-4-yl)acetonitrile (2.14 g) (see Preparation 31). The title compound was obtained as a white solid (1.94 g, 82.5%), m.p. 193°-195° C.

Analysis %: Found: C,65.40; H,5.47; N,20.96.
C$_{11}$H$_{11}$N$_3$O requires: C,65.66; H,5.50; N,20.88.

PREPARATION 29

(RS) 2-Phenyl-2-(1H-pyrazol-3(5)-yl)acetamide

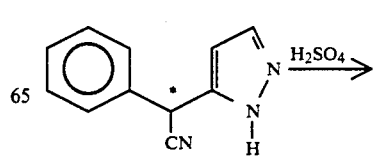

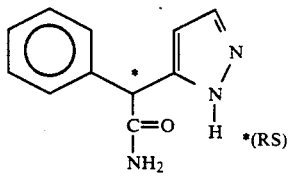

This was obtained by a similar method to that described in Preparation 27 using (RS) 2-phenyl-2-(1H-pyrazol-3(5)-yl)acetonitrile (3 g) (see Preparation 32). The title compound was obtained from dichloromethane as a white solid (2.33 g, 71%), m.p. 65°–67° C.

Analysis %: Found: C,64.00; H,5.38; N,20.08. $C_{11}H_{11}N_3O \cdot \tfrac{1}{4}H_2O$ requires: C,64.21; H,5.63; N,20.42.

PREPARATION 30

(RS) 2-(1H-Imidazol-4(5)-yl-2-phenylacetonitrile

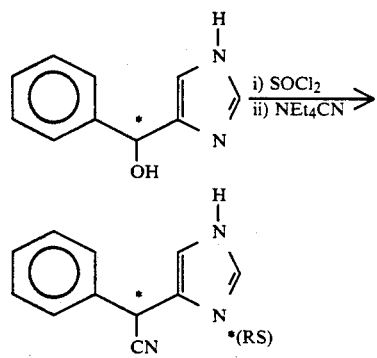

(RS) 2-(1H-Imidazol-4(5)-yl)-2phenylmethanol (see Preparation 33) (3.74 g) was added to thionyl chloride (35 ml) at 0° C., stirred for 45 minutes, and evaporated under reduced pressure to leave an oily residue. Chloroform (30 ml) was twice added to, and then evaporated from, the residue, and the residue at 0° C. in dichloromethane (50 ml) was then treated with tetraethylammonium cyanide (11.14 g) in dichloromethane (150 ml). After 15 minutes at 0° C. and 30 minutes at room temperature, the solvent was evaporated and the residue was partitioned between ethyl acetate and saturated aqueous sodium bicarbonate solution. The organic layer was dried over magnesium sulphate and the residue, after evaporation, was purified by chromatography on silica gel with ethyl acetate as eluant, to give, after evaporation of appropriate fractions and crystallisation from ethyl acetate, the title compound as a white solid (1.69 g, 51.4%), m.p. 124°–126° C.

Analysis %: Found: C,71.94; H,4.89; N,22.94. $C_{11}H_9N_3$ requires: C,72.11; H,4.95; N,22.94.

PREPARATION 31

(RS) 2-Phenyl-2-(1H-pyrazol-4-yl)acetonitrile

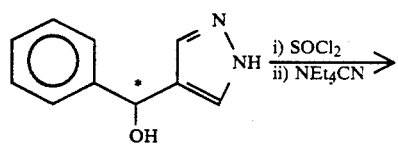

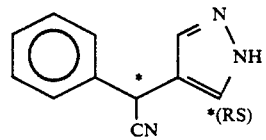

This was obtained by a similar method to that described in Preparation 30 using (RS) 2-phenyl-2-(1H-pyrazol-4-yl)methanol (prepared as described in Bull. Soc. Chim. France, 2764, 7, 1972) (3 g). The title compound, as a white solid, was obtained by chromatography on silica gel using ether/dichloromethane (50:50) as eluant (2.2 g, 60%), m.p. 124°–127° C.

Analysis %: Found: C,72.00; N,4.95; N,22.86. $C_{11}H_9N_3$ requires; C,72.11; H,4.95; N,22.94.

PREPARATION 32

(RS) 2-Phenyl-2-(1H-pyrazol-3(5)-yl)acetonitrile

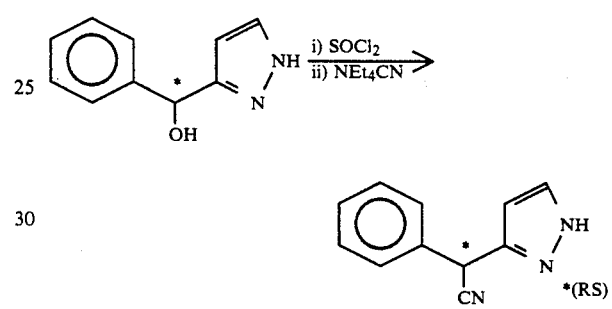

This was obtained by a similar method to that described in Preparation 30 using (RS) 2-phenyl-2-(1H-pyrazol-3(5)-yl)methanol (prepared as described in Bull. Soc. Chim. France, 2764, 7, 1972) (3.8 g) instead of (RS) (1H-imidazol-3(5)-yl)phenylmethanol. The title compound, as a white solid, was obtained by chromatography on silica gel using ether/dichloromethane (50:50) as eluant (3 g, 75%), m.p. 57°–60° C.

Analysis %: Found: C,71.94; H,4.87; N,22.96. $C_{11}H_9N_3$ requires: C,72.11; H,4.95; N,22.94.

PREPARATION 33

(RS) 1-(1H-Imidazol-4(5)-yl)-1-phenylmethanol hydrochloride

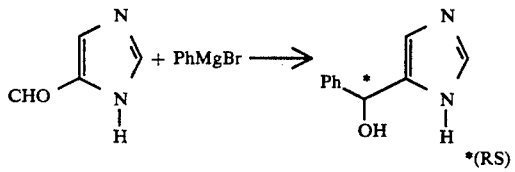

Imidazole-4(5)-carboxaldehyde (prepared as described in J. Pharm. Soc. Japan 76, 1101, 1956) (2.9 g) in tetrahydrofuran (180 ml) was added to phenyl magnesium bromide (23.6 ml of a 3M solution in ether) in tetrahydrofuran (40 ml) at 0° C. After 18 hours saturated aqueous ammonium chloride solution was added and the mixture was extracted with ethyl acetate. The organic layer was dried over magnesium sulphate and the residue, after evaporation, was purified by chromatography on silica gel by gradient elution using dichloromethane plus 0→2% methanol as the eluant to give, after evaporation of appropriate fractions and treatment with ethereal hydrogen chloride, the title compound (3.1 g, 59%), m.p. 146° C.

Analysis %: Found: C,56.73; H,5.13; N,12.99. C$_{10}$H$_{10}$N$_2$O.HCl requires: C,57.01; H,5.26; N,13.29.

We claim:

1. A compound having the formula

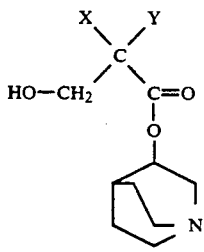

I wherein
X is either
(a) a phenyl group optionally sustituted by 1 or 2 substituents each independently selected from halo, CF$_3$, C$_1$-C$_4$ alkyl, C$_1$-C$_4$ alkoxy and hydroxy, or
(b) a thienyl group;
and
Y is a 5-membered nitrogen-containing heterocyclic group which is attached to the adjacent carbon atom either by a carbon or a ring nitrogen atom and is selected from imidazolyl, pyrazolyl, triazolyl and tetrazolyl, Y being optionally substituted by 1 or 2 substituents each independently selected from halo, CF$_3$, C$_1$-C$_4$ alkozy, hydroxy and amino;
and pharmaceutically acceptable salts thereof.

2. A compound as claimed in claim 1 wherein X is either
(a) a phenyl group optionally substituted by 1 or 2 fluorine atoms, or
(b) a 3-thienyl group;
and
Y is an unsubstituted heterocyclic group as defined in claim 1.

3. A compound as claimed in claim 2 wherein X is an unsubstituted phenyl group and Y is 1H-imidazol-1-yl, 1H-1,2,3-triazol-1-yl, 1H-1,2,4-triazol-1-yl, 1H-pyrazol-1-yl, 1H-tetrazol-1-yl, 1H-imidazol-4(5)-yl, 1H-pyrazol-4-yl, or 1H-pyrazol-3-(5)-yl.

4. A compound as claimed in claim 3, wherein X is an unsubstituted phenyl group and Y is 1H-imidazol-1-yl.

5. A compound as claimed in claim 1 wherein the stereochemistry at each of the two asymmetric centers has the R configuration, said compound being (2R,3'R)-3-quinuclidinyl-3-hydroxy-2-(1H-imidazol-1-yl)-2-phenylpropanoate having the formula

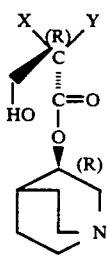

IA wherein X and Y are as defined in claim 1.

6. A compound according to claim 2 wherein the stereochemistry at each of the two asymmetric centers has the R configuration, said compound having the formula

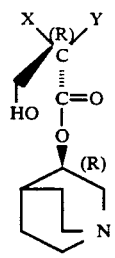

IA wherein X and Y are as defined in claim 1.

7. A compound according to claim 3 wherein the stereochemistry at each of the two asymmetric centers has the R configuration, said compound having the formula

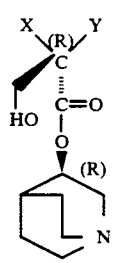

IA wherein X and Y are as defined in claim 3.

8. A compound according to claim 4 wherein the stereochemistry at each of the two asymmetric centers has the R configuration, said compound having formula

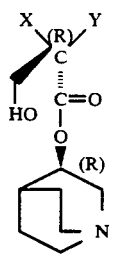

IA wherein X and Y are as defined in claim 4.

9. A pharmaceutical composition for the treatment of a condition selected from chronic obstructive airways disease and asthma comprising an amount of a compound of claim 1 effective in treating such condition and a pharmaceutically acceptable carrier.

10. A method to treating a condition selected from chronic obstructive airways disease and asthma, comprising administering to a patient in need of such treatment an amount of a compound according to claim 1 effective in treating such condition.

11. A compound having the formula:

II

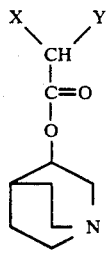

wherein
X is either (a) a phenyl group optionally substituted by 1 or 2 substituents each independently selected from halo, $CF_3$, $C_1$-$C_4$ alkyl, $C_1$-$C_4$ alkoxy and hydroxy, or
(b) a thienyl group;
and
Y is a 5-membered nitrogen-containing heterocyclic group attached to the adjacent carbon atom either by a carbon or a ring nitrogen atom and which is selected from imidazolyl, pyrazoly, triazolyl and tetrazolyl, Y being optionally substituted by 1 or 2 substituents each independently selected from halo, $CF_3$, $C_1$-$C_4$ alkoxy, hydroxy and amino.

* * * * *